United States Patent [19]

Schnur

[11] 4,283,539
[45] Aug. 11, 1981

[54] ISOQUINOLINE ACETIC ACIDS

[75] Inventor: Rodney C. Schnur, Noank, Conn.

[73] Assignee: Pfizer Inc., New York, N.Y.

[21] Appl. No.: 104,939

[22] Filed: Dec. 18, 1979

[51] Int. Cl.³ .................... C07D 217/16; A61K 31/47
[52] U.S. Cl. ................................... 546/141; 546/142; 546/143; 424/258
[58] Field of Search ...................... 546/141, 143, 142; 424/258

[56] References Cited

U.S. PATENT DOCUMENTS 4,036,964 7/1977 Buckle et al. ........................ 546/141

OTHER PUBLICATIONS

Maeda et al. Japan Kokai 75 36,470 Apr. 5, 1975, Chem. Abstracts 83 97051S (1975).

Primary Examiner—Donald G. Daus
Assistant Examiner—David B. Springer
Attorney, Agent, or Firm—Charles J. Knuth; Peter C. Richardson

[57] ABSTRACT

Novel isoquinoline acetic acids and derivatives thereof useful as aldose reductase inhibitors and as therapeutic agents for the treatment of chronic diabetic complications, especially diabetic cataracts are disclosed. Also disclosed are pharmaceutical compositions containing the novel compounds of this invention and a method of treatment of diabetic cataracts by administration of effective amounts of the novel compounds described herein.

13 Claims, No Drawings

ISOQUINOLINE ACETIC ACIDS

BACKGROUND OF THE INVENTION

This invention relates to novel isoquinoline acetic acids and derivatives thereof useful in the treatment of certain chronic complications arising from diabetes mellitus, especially diabetic cataracts, to pharmaceutical compositions containing such compounds and to a method of treatment of diabetic cataracts by use of these compounds.

In the past various attempts have been made to obtain new anti-diabetic agents. Generally these efforts have involved synthesis of new organic compounds, particularly sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1,3-dioxo-1H-benz[d,e]-isoquinoline-2(3H)-acetic acid and derivatives thereof to be useful for the treatment of these conditions. Such aldose reductase inhibitors function by inhibiting the activity of the enzyme aldose reductase, which is primarily responsible for regulating the reduction of aldoses, such as glucose and galactose to the corresponding polyols, such as sorbitol and galacticol, in humans and other animals. In this way, unwanted accumulations of galacticol in the lens of galactosemic subjects and of sorbitol in the lens, peripheral nervous cord and kidney of various diabetic subjects are prevented or reduced. Accordingly, such compounds are of therapeutic value as aldose reductase inhibitors for controlling certain chronic diabetic complications, especially those of an ocular nature, since it is known in the art that the presence of polyols in the lens of the eye leads to cataract formation with a concomittant loss of lens clarity.

SUMMARY OF THE INVENTION

The present invention relates to novel aldose reductase inhibitors useful as therapeutic agents for preventing or alleviating chronic diabetic complications, especially diabetic cataracts. Specifically, the compounds of the present invention are novel isoquinoline acetic acids of the formulae:

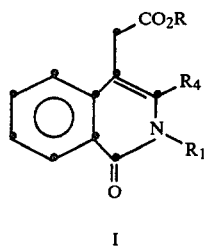

I

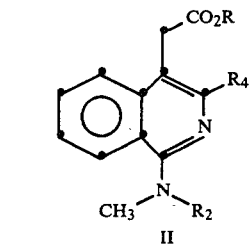

II and

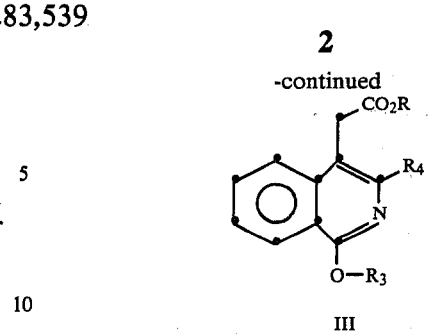

III wherein R is selected from the group consisting of hydrogen and alkyl of 1 to 3 carbon atoms; $R_1$ is selected from the group consisting of $-CH_2X$ and $-OCH_2X$; $R_2$ is $-CH_2X$; $R_3$ is selected from the group consisting of $-X$ and $-CH_2X$; and $R_4$ is selected from hydrogen and methyl; wherein X is selected from the group consisting of phenyl, monosubstituted and disubstituted phenyl, said substituents being selected from the group consisting of chloro, bromo and fluoro; and the pharmaceutically acceptable salts thereof.

R is preferably hydrogen or methyl, $R_4$ is preferably methyl and X is preferably phenyl, monochloro- or dichlorophenyl.

One group of compounds of interest is that of formula I, including those compounds where $R_1$ is $-OCH_2X$ or $-CH_2X$ wherein X is 3,4-dichlorophenyl and where R is preferably hydrogen and $R_4$ is preferably methyl.

A further group of compounds of interest is that of formula II, especially where $R_2$ is $-CH_2X$ and X is phenyl or 4-chlorophenyl, preferably where R is hydrogen and $R_4$ is methyl.

Also of interest are compounds of formula III, especially those wherein $R_3$ is $-X$ or $-CH_2X$ and X is phenyl, 4-chlorophenyl or 3,4-dichlorophenyl, especially where R is hydrogen and $R_4$ is methyl.

Also embraced by the present invention are pharmaceutical compositions comprising a pharmaceutically acceptable carrier and a compound of formula I, II or III in an amount effective for the treatment of diabetic cataracts. Preferred compounds for use in such pharmaceutical compositions are those having the preferred substituents for R, $R_1$, $R_2$, $R_3$, $R_4$ and X as defined herein above. Preferred pharmaceutical compositions are those in the form of an ophthalmic preparation.

The present invention further comprises a method of treatment for diabetic cataracts comprising administering to a subject in need of treatment an effective amount of a compound of formula I, II or III, preferably a compound having the preferred substituents for R, $R_1$, $R_2$, $R_3$, $R_4$ and X as defined herein above.

DETAILED DESCRIPTION OF THE INVENTION

The compounds of formulae I, II and III are readily prepared from the appropriate known 2-$R_4$-1-oxo-3-indane acetic acid, see Bull. Soc. Chim. Fr., 1970, 1143. Thus for example, these starting materials may be synthesized from the known compounds 3-phenylglutaric acid (Braun et al., Chem. Ber. 64B, 1785 (1931)) when $R_4$ is to be hydrogen, or 2-phenyl-butane-1,3-dicarboxylic acid (Swan, J. Chem. Soc. 1955, 1039) when $R_4$ is to be methyl. The appropriate dicarboxylic acid is heated in a strong acid such as concentrated sulfuric acid, p-toluene sulfonic acid, phosphorous acid and the like at a temperature from about 75° C. to about 150° C., preferably from about 90° C. to 120° C., for a period from about 12 to 30 hours, preferably about 20 to 24 hours.

The preparation of compounds of formula I is illustrated by reference to reaction Scheme A. Compounds of formula I wherein $R_1$ is —$OCH_2X$ may be prepared by first converting the 2-$R_4$-1-oxo-3-indane acetic acid (1) to its lower alkyl ester (2) having from 1 to 3 carbon atoms in the alkyl group, by conventional esterification methods, for example by reaction with a diazoalkane, or by heating with the appropriate alcohol in the presence of a catalytic amount of an acid, such as sulfuric acid, p-toluene sulfonic acid and the like. Preferably, the methyl ester is formed by reaction of the 2-$R_4$-1-oxo-3-indane acetic acid with diazomethane in an inert organic solvent such as diethyl ether or isopropyl ether at a temperature from about −10° C. to about 20° C., preferably from about 0° C. to 10° C.

The 2-$R_4$-1-oxo-3-indane acetic acid alkyl ester (2) is then reacted with an alkyl nitrite, preferably n-butyl nitrite or isoamyl nitrite to form a 1,2-dihydro-2-hydroxy-3-$R_4$-1-oxo-4-isoquinoline acetic acid alkyl ester (3) the reaction is generally conducted in a polar organic solvent such as an n-alkanol of 1 to 4 carbon atoms, dimethylformamide, dimethylsulfoxide and the like, in the presence of an alkali metal alkoxide. A preferred solvent is methanol and preferred alkali metal alkoxides are sodium and potassium methoxides. The reaction is generally conducted at a temperature from about 0° C. to 80° C., preferably from about 20° C. to 30° C.

REACTION SCHEME A

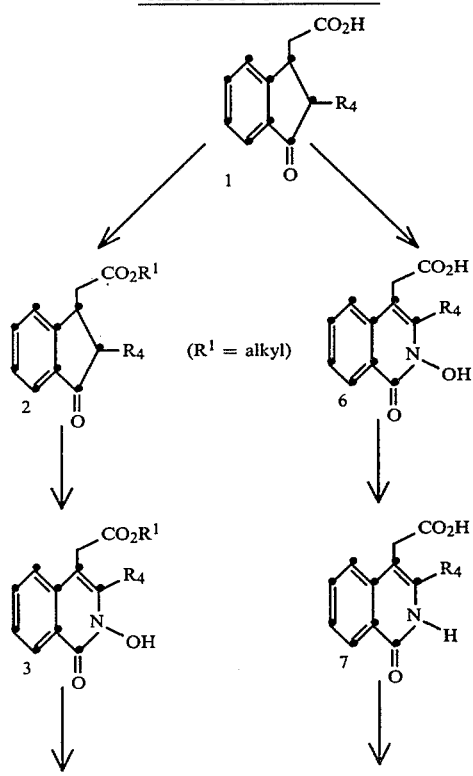

-continued
REACTION SCHEME A

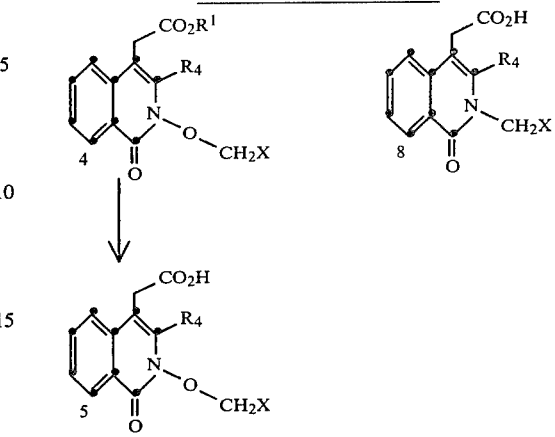

The 1,2-dihydro-2-hydroxy-3-$R_4$-1-oxo-4-isoquinoline acetic acid alkyl ester (3) is reacted with an appropriately substituted benzyl halide, $ClCH_2X$ or $BrCH_2X$, where X is as previously defined, in the presence of a base such as an alkali metal alkoxide, hydroxide or hydride, preferably an alkali metal alkoxide such as potassium t-butoxide or the like. The reaction is generally conducted at a temperature from about 10° C. to about 80° C., preferably from about 20° C. to 30° C., in an organic solvent such as an n-alkanol of 1 to 4 carbon atoms, preferably methanol or ethanol, or in dimethylformamide, dimethylsulfoxide, benzene, ethers such as dioxane, tetrahydrofuran and the like. The alkyl ester of formula I (4) so obtained is readily converted to the free acid (5) by base hydrolysis, for example in the presence of an alkali metal hydroxide in aqueous solution at a temperature from about 0° C. to 70° C., preferably from about 20° C. to about 35° C.

Compounds of formula I where $R_1$ is —$CH_2X$ are formed by reaction of the free acid, 2-$R_4$-1-oxo-3-indane acetic acid (1) with an alkyl nitrite under the conditions previously described for the conversion of the alkyl ester (2) to (3), preferably using an n-alkanol solvent, to form the 1,2-dihydro-2-hydroxy-3-$R_4$-1-oxo-isoquinoline acetic acids (6). Reaction of the latter with a phosphorous trihalide, such as phosphorous trichloride or phorphorous tribromide, affords the 1,2-dihydro-3-$R_4$-1-oxo-4-isoquinoline acetic acid (7). The reaction is conducted in an aprotic organic solvent, preferably a lower alkyl acetate such as ethyl acetate, at a temperature from about 50° C. to 120° C. preferably about 60° C. to 90° C. In this preferred temperature range, relatively short reaction times of about 1 to 3 hours will allow formation of the desired 1,2-dihydro-3-$R_4$-1-oxo-4-isoquinoline acetic acid (7). Heating for relatively longer times, for example from 14 to 24 hours, allows further reaction to form a 1-halo-3-$R_4$-4-isoquinoline acetic acid ((9) in reaction scheme B), which, as will be more fully described hereinafter, are useful in the preparation of compounds of formula II and III. Compounds of formula I where $R_1$ is —$CH_2X$ (8) are formed by reaction of the 1,2-dihydro-3-$R_4$-1-oxo-4-isoquinoline acetic acid (7) with an appropriately substituted benzyl halide, $ClCH_2X$ or $BrCH_2X$, wherein X is as previously defined, in the presence of a base such as an alkali metal hydride, for example sodium hydride. The reaction is conducted in an organic solvent such as dimethylformamide, toluene, xylene, or the like, at a temperature from about 50° C. to about 150° C., preferably from about 100° to 120° C.

REACTION SCHEME B

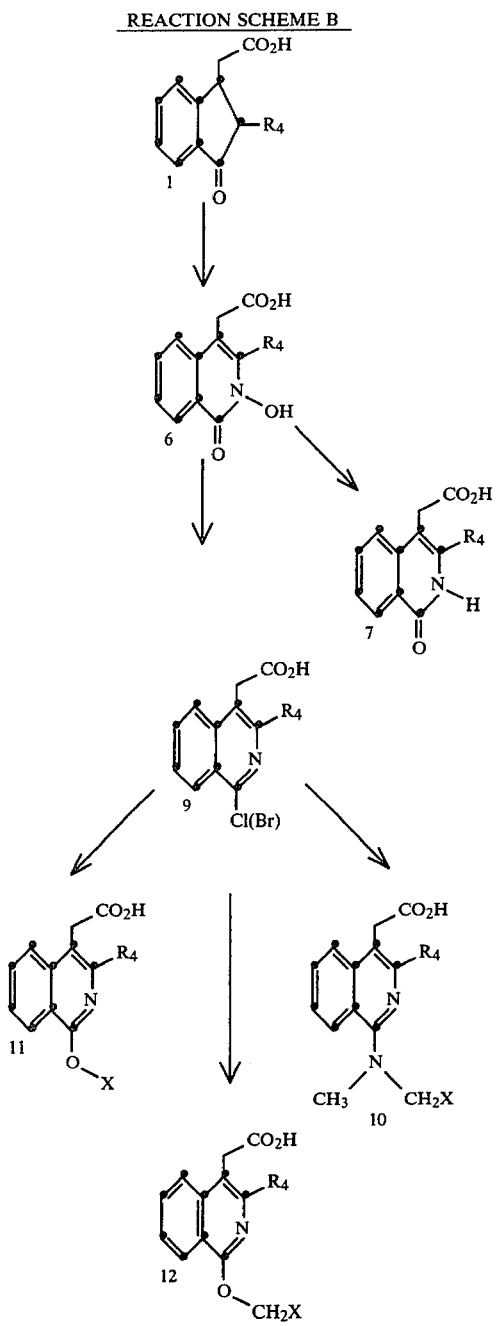

The preparation of compounds of formulae II and III is described with reference to reaction scheme B. Compounds of formula II and III are prepared from the 2-$R_4$-1-oxo-3-indane acetic acids (1) via the 1,2-dihydro-2-hydroxy-3-$R_4$-isoquinoline acetic acid (6) prepared by the reaction of (1) with an alkyl nitrite, as previously described. As noted previously, the 1,2-dihydro-2-hydroxy-3-$R_4$-isoquinoline acetic acid (6) may be converted directly to the 1-halo-3-$R_4$-4-isoquinoline acetic acid (9) by heating with a phorphorous trihalide, such as phosphorous trichloride or phosphorous tribromide at a temperature from about 50° C. to 120° C., preferably from about 60° to 90° C., in an aprotic organic solvent, preferably a lower alkyl acetate such as ethyl acetate, for relatively long reaction times, for example from about 14 to 24 hours. Alternatively, by conducting the reaction under the same conditions but for relatively short reaction times, for example from about 1 to 3 hours. The 1,2-dihydro-3-$R_4$-1-oxo-4-isoquinoline acetic acid (7) may be isolated. The 1-halo-3-$R_4$-4-isoquinoline acetic acid (9) is then formed by reaction of 1,2-dihydro-3-$R_4$-1-oxo-4-isoquinoline acetic acid (7) with a phosphorous oxyhalide, such as phosphorous oxychloride or phosphorous oxybromide, in an organic solvent such as a lower alkyl acetate, for example ethyl acetate, at a temperature from about 50° C. to 150° C., preferably from about 100° to 120° C.

Compounds of formula II (10) are then produced by the reaction of the 1-halo-3-$R_4$-4-isoquinoline acetic acid (9) with an appropriately substituted N-methylbenzylamine. The reaction is generally conducted in an organic solvent such as an ether like dioxane or tetrahydrofuran, or in dimethylformamide or toluene, and the like, at a temperature from about 50° C. to about 150° C., preferably at the reflux temperature of solvent.

Compounds of formula III where $R_3$ is —X (11) or —$CH_2X$ (12) are formed, respectively, by the reaction of an appropriately substituted phenol or benzyl alcohol with the 1-halo-3-$R_4$-4-isoquinoline acetic acid (9) in the presence of a base, preferably an alkali metal alkoxide, such as sodium or potassium t-butoxide. The reaction is generally conducted in an organic solvent, such as dimethylformamide, toluene, xylene and the like, at a temperature of about 50° C. to 150° C., preferably from about 100° to 120° C.

Compounds of formula I, II and III where R is alkyl of 1 to 3 carbon atoms are readily produced from the free acids by conventional esterification methods, for example by reaction with the appropriate alcohol under acid catalyzed conditions, or by reaction with the appropriate diazoalkane.

Pharmaceutically acceptable salts can be readily prepared from compounds of formulae I, II or III, wherein R is hydrogen by conventional methods such that the acidic hydrogen is replaced by a suitable cation. Thus, these salts may be readily prepared by treating the isoquinoline acetic acids with an aqueous solution of the desired pharmaceutically acceptable cations, for example a solution of the hydroxide or carbonate, and evaporating the resulting solution to dryness, preferably under reduced pressure. Alternatively, a lower alkanol solution of the carboxylic acid of formula I, II or III may be mixed with an alkoxide of the desired metal and the solution evaporated to dryness. Suitable pharmaceutically acceptable salts include, but are not limited to those having potassium, sodium, ammonium, calcium, or magnesium as the cation. In addition, compounds of formula II and III of this invention may form acid addition salts by reaction with a pharmaceutically acceptable acid to form, for example the hydrochloride, hydrobromide, sulfate, bisulfate, lactate, oxalate, citrate, and the like. The use of the term pharmaceutically acceptable salts in the specification and claims thereof is meant to embrace both the metal salts and the acid addition salts of the compounds of this invention as described hereinabove.

The novel isoquinoline acetic acids of formula I, II and III are useful as aldose reductase inhibitors and as such are of therapeutic value in the treatment of chronic complications associated with diabetes, especially in the treatment of diabetic cataracts. As used in the specification and claims hereof, treatment is meant to include both prevention and alleviation of such conditions. For the treatment of diabetic cataracts the compounds of this invention are administered to the eye of the subject in need of treatment in the form of an ophthalmic preparation prepared in accordance with conventional pharmaceutical practice, see for example "Remington's Pharmaceutical Sciences", 15th Edition, pages 1488 to 1501 (Mack Publishing Co., Easton, Pa.). The ophthalmic preparation will contain a compound of formula I, II or III, or a pharmaceutically acceptable salt thereof, in a concentration from about 0.1 to about 5% by weight, preferably from about 0.5 to about 2%, in a pharmaceutically acceptable solution, suspension or ointment. Some variation in concentration will necessarily occur depending on the particular compounds employed, the condition of the subject to be treated and the like, and the person responsible for treatment will determine the most suitable concentration for the individual subject. The opthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like. Suitable preservatives include benzalkonium chloride, benzethonium chloride, chlorobutanol, thimerosal and the like. Suitable buffers include boric acid, sodium and potassium bicarbonate, sodium and potassium borate, sodium and potassium carbonate, sodium acetate, sodium biphosphate and the like, in amounts sufficient to maintain the pH at between about 6 and 8, preferably between abour 7 and 7.5. Suitable tonicity agents are dextran 40, dextran 70, dextrose, glycerin, potassium chloride, propylene glycol and sodium chloride and the like, such that the sodium chloride equivalent of the opthalmic solution is in the range 0.9 plus or minus 0.2 percent. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethyl propylcellulose, lanolin, methyl cellulose, petrolatem, polyethylene glycol, polyvinyl alcohol, polyvinyl pyrrolidone, carboxymethylcellulose and the like. The ophthalmic preparation will be administered topically to the eye of the subject in need of treatment by conventional methods, e.g. in the form of drops or by bathing the eye in the ophthamic solution.

The activity of the compounds of this invention as aldose reductase inhibitors and as agents for the treatment of diabetic cataracts may be determined by standard pharmacological tests. Such tests include, for example, measuring their ability to inhibit the enzyme activity of isolated aldose reductase, following the general procedure described in U.S. Pat. No. 3,821,383 and based on the procedure of Hayman et al., J. Biol. Chem. 240, 877 (1965). Based on the activity of the compounds of this invention in this test, it is expected that the compounds will also show activity as aldose reductase inhibitors when tested at suitable concentrations in other standard pharmacological tests, for example those measuring their ability to reduce or inhibit sorbitol accumulation in the sciatic nerve of acutely streptozotocinized (i.e. diabetic) rats; measuring their ability to reverse already-elevated sorbitol level in the sciatic nerve and lens of chronic streptozotocin-induced diabetic rats; measuring their ability to prevent or inhibit galacticol formation in the lens of acutely galatosemic rats; and measuring their ability to delay cataract formation and reduce the severity of lens opacities in chronic galactosemic rats.

It is also expected that the compounds of the present invention will be useful in the treatment of other chronic diabetic complications such as retinopathy and neuropathy. For treatment of such conditions the compounds of this invention will be administered, either alone or in combination with pharmaceutically acceptable carriers or diluents, in dosages of about 5 to 250 mg./kg. body weight of the subject in need of treatment per day. However, some variation in dosage will necessarily occur depending on the condition of the subject being treated and the particular compound employed and the physician will, in any event, determine the appropriate dose for the individual subject. Suitable pharmaceutical carriers or diluents for this purpose includes inert solid diluents or fillers, sterile aqueous solutions or suspensions and various organic solvents in accord with standard pharmaceutical practice. Such pharmaceutical compositions are then readily administered in a variety of dosage forms by oral or parenteral routes of administration. If desired, the pharmaceutical compositions can contain other ingredients such as excipients, flavorants, binders and the like.

The present invention is illustrated by the following examples. It will be understood, however, that the invention is not limited to the specific details of these examples. In the following examples, all temperatures are in degrees centigrade.

EXAMPLE 1

2-Methyl-1-oxo-3-indane Acetic Acid

2-Phenylbutane-1,3-dicarboxylic acid (Swan, J. Chem. Soc., 1955, 1039) (20.0 g, 90.0 mmol) was dissolved in 300 ml. concentrated sulfuric acid and heated at 100° for 24 hr. The hot solution was poured onto 1 kg ice and the mixture extracted with 5×250 ml. ether. The ether phases were washed with brine, dried over magnesium sulfate, filtered, and vacuum evaporated to yield a pale yellow syrup 14.6 g. (79%), m/e 222. The NMR spectrum indicated the presence of only one major isomer as evidenced by a single upfieled doublet, assigned to the 2-methyl substituent, and small amounts of three other isomers.

EXAMPLE 2

Methyl 2-Methyl-1-oxo-3-indane Acetate

Solid 2-methyl-1-oxo-3-indane acetic acid (1.00 g., 4.9 mmol) was added to an ethereal solution of excess diazomethane formed from N-methyl-N'-nitro-N-nitrosoquanidine (3.16 g., 14.7 mmol) (Aldrich) and 7.5 ml. of 40% potassium hydroxide in 25 ml. ether at 0° C. After 45 minutes acetic acid was added sufficient to discharge the unreacted diazomethane. The solution was washed with 5×50 ml. saturated sodium bicarbonate and 2×50 ml brine, dried over magnesium sulfate, filtered and evaporated in vacuo to a solid 1.057 g. (99%) mp 70°–72° C. Recrystallization from hexane gave material with mp 74°–76°.

EXAMPLE 3

Methyl 1,2-Dihydro-2-hydroxy-3-methyl-1-oxo-4-isoquinoline Acetate

A clear yellow solution of methyl 2-methyl-1-oxo-3-indane acetic acid (0.844 g., 3.87 mmol) and n-butyl nitrite (1.1 ml., 9.7 mmol) [W. A. Noyes, Org. Syn., Col. Vol. II, 108 (1943)] in 7.6 ml methanol was stirred as a 5% solution of sodium methoxide in methanol. (1.2 ml., 2.6 mmol) was added. Addition of 25 ml. ether to this red-brown solution followed by 1 N hydrochloric acid to pH 3–4 precipitated the title compound which was washed with water and ether and dried: 0.40 g. (42%) mp 185°–190°.

EXAMPLE 4

2-(3,4-Dichlorobenzyloxy)-1,2-dihydro-3-methyl-1-oxo-4-isoquinoline Acetic Acid

Methyl 1,2-Dihydro-2-hydroxy-3-methyl-1-oxo-4-isoquinoline acetate (0.300 g., 1.21 mmol) suspended in 2 ml. ethanol was reacted with potassium tert-butoxide (0.136 g., 1.21 mmol) (Aldrich). The solid dissolved upon warming. After cooling to room temperature 3,4-dichlorobenzylchloride (0.130 ml., 1.21 mmol) (Pfaltz and Bauer) was added and the mixture was stirred overnight. The residue obtained after vacuum evaporation was taken up in ethyl acetate/hexane and filtered. This mother liquor after evaporation in vacuo gave a solid crude ester (256 mg., 52%, mp 90°–94°) which was hydrolyzed for 24 hr in 6.3 ml. of 5:1 dioxane:water containing 1 equivalent of sodium hyroxide. The title compound was obtained upon acidification with 1 N hydrochloric acid and filtration; 215 mg., 45% overall, mp 222° dec.

EXAMPLE 5

1,2-Dihydro-2-hydroxy-3-methyl-1-oxo-4-isoquinoline Acetic Acid

2-Methyl-indan-1-one-3-acetic acid (1.00 g., 4.90 mmol) dissolved in 10 ml. methanol and n-butyl nitrite (W. A. Noyes, Org. Syn. Col. Vol. II, p. 108, 1943) (1.38 ml., 12.20 mmol) was stirred at room temperature while 4.5 ml. of 5% sodium methoxide in methanol (9.8 mmol) was added. The solution became orange-red and upon dilution with ether (50 ml.) and filtration yielded a light orange precipitate. The solid was taken up in water and acidified with 6 N hydrochloric acid to precipitate the title compound; 0.76 g. (67%). Recrystallization from dioxane/hexane gave material of mp 198°–200°.

EXAMPLE 6

1,2-Dihydro-3-methyl-1-oxo-4-isoquinoline Acetic Acid 1,2-Dihydro-2-hydroxy-3-methyl-1-oxo-4-isoquinoline acetic acid (4.0 g., 17.2 mmol) dissolved in 30 ml. ethyl acetate at 0° was reacted with phosphorous trichloride (1.50 ml., 17.2 mmol). The mixture was heated at 80° for 1.5 hr then poured onto 100 g. of ice water, stirred for 16 hr and filtered yielding a light yellow crude product; 3.307 mg (89%) mp 280°–295° d. Recrystallization from acetic acid afforded analytically pure material of mp 295°–300° d.

EXAMPLE 7

2-(3,4-Dichlorobenzyl)-1,2-dihydro-3-methyl-1-oxo-4-isoquinoline Acetic Acid

Sodium hydride (48 mg., 2.0 mmol) (Ventron, washed free of mineral oil with hexane) and 2 ml. dimethylformamide were reacted with 1,2-dihydro-3-methyl-1-oxo-4-isoquinoline acetic acid (217 mg., 1.0 mmol). After homogeneity was observed, 3,4-dichlorobenzyl chloride (196 mg., 1.0 mmol) in 1 ml. dimethylformamide was added. The mixture was heated at 110° for 3 hr, cooled and partitioned between hydrochloric acid and ethyl acetate. The crude product obtained from the organic layer after several aqueous washings, drying over magnesium sulfate, filtration, and vacuum evaporation was column chromatographed on silica gel with ethyl acetate; 104 mg., 28%, mp 218°–220°.

EXAMPLE 8

1-(3,4-Dichlorobenzyloxy)-3-methyl-4-isoquinoline Acetic Acid 1,2-Dihydro-3-methyl-1-oxo-4-isoquinoline acetic acid (770 mg., 3.30 mmol) and phosphorous oxychloride (1.0 ml. 10.7 mmol) were refluxed in 8 ml. ethyl acetate for 16 hr then vacuum evaporated to dryness. The residue was partitioned between water and ethyl acetate. The aqueous phase was washed with ether. The combined organic phases were washed with brine, dried over magnesium sulfate, filtered, and vacuum evaporated to yield a viscous, homogeneous oil, 1-chloro-3-methyl-4-isoquinoline acetic acid; 772 mg. (99%). This oil (623 mg., 2.65 mmol) in 6 ml. dimethylformamide was added to a solution of 3,4-dichlorobenzyl alcohol (2.75 g., 15.5 mmol) and potassium tert-butoxide (600 mg., 534 mmol) in 2 ml. dimethylformamide and the mixture was heated at 115° for 3 hr. After cooling the mixture was poured onto crushed ice and washed with 3×60 ml. ether. The basic aqueous layer was acidified to pH 3 with 1 N hydrochloric acid and extracted 3×100 ml. ether. The organic extract was dried over magnesium sulfate, filtered, and vacuum evaporated to an oily solid; 568 mg. (57%). Trituration of this residue with methanol then hexane and fractional crystallization from chloroform afforded pure title compound: 44 mg. (4%), mp 180°–183°.

EXAMPLE 9

1-(4-Chlorophenoxy)-3-methyl-4-isoquinoline Acetic Acid

A mixture of 1-chloro-3-methyl-4-isoquinoline acetic acid (237 mg., 1.01 mmol) prepared as in Example 8, 4-chlorophenol (260 mg., 2.02 mmol), and potassium tert-butoxide (226 mg., 2.02 mmol) were heated at 100° for 3 hr. After cooling the mixture was diluted with ethyl acetate and water and acidified to pH 1–2. The separated aqueous phase was extracted with 20 ml. ethyl acetate. The combined organic phases were washed with brine, dried over magnesium sulfate, filtered, and vacuum evaporated to a brown oil. Chromatography of this on silica gel eluted with ethyl acetate gave a pale yellow solid; 80 mg., 24%, mp 192°–195° d.

EXAMPLE 10

1-(N-4-Chlorobenzyl-N-methyl-amino)-3-methyl-4-isoquinoline Acetic Acid Hydrochloride N-Methyl-4-chlorobenzylamine (1.40 g., 9.0 mmol) and 1-chloro-3-methyl-4-isoquinoline acetic acid (770 mg., 3.0 mmol), prepared as in Example 8, were refluxed in 20 ml. p-dioxane for 16 hr. The cooled reaction mixture was partitioned between 200 ml ether and 50 ml 1 N sodium hydroxide. The ether rafinate was extracted with $2 \times 30$ ml 1 N sodium hydroxide. The combined basic phases were acidified to pH 6.5 with 6 N hydrochloric acid and extracted with $3 \times 75$ ml ethyl acetate. This organic phase was dried over magnesium sulfate, filtered, and vacuum evaporated to an oily residue. Chromatography of this on silica gel eluted with ethyl acetate gave an oil. The title compound was prepared from this oil by treatment with hydrochloric acid gas in ether, filtrate, and drying in vacuo; 52 mg. (4%), m/e 354.

EXAMPLE 11

The compounds produced in Examples 4, 7, 8, 9 and 10 were tested for their ability to reduce or inhibit aldose reductase enzyme activity, following the procedure described in U.S. Pat. No. 3,821,383 and based on the procedure of Hayman et. al., Journal of Biological Chemistry, 240, 877 (1965). The substrate employed was partially purified aldose reductase enzyme obtained from calf lens. The results obtained with each compound at a concentration of $10^{-4}$ M and $10^{-5}$ M are expressed as percent inhibition of enzyme activity.

| Compound of Example | % Inhibition at $10^{-4}$M | % Inhibition at $10^{-5}$M |
| --- | --- | --- |
| 4 | 90 | 77 |
| 7 | 27 | — |
| 8 | 83 | 95 |
| 9 | 95 | 91 |
| 10 | 99 | 97 |

I claim:

1. A compound selected from the group consisting of those of the formulae

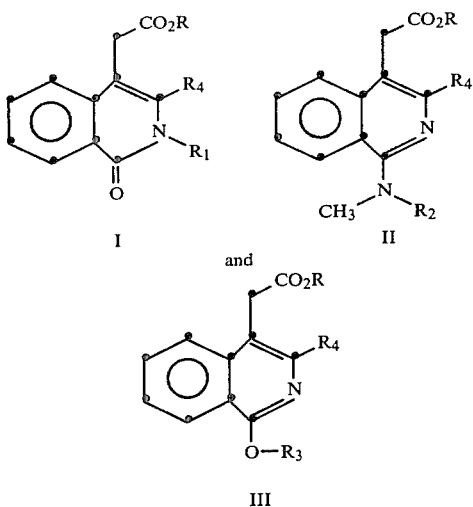

wherein
R is selected from the group consisting of hydrogen and alkyl of 1 to 3 carbon atoms;
$R_1$ is selected from the group consisting of —$CH_2$—X and —O—$CH_2$—X;
$R_2$ is —$CH_2$—X;
$R_3$ is selected from the group consisting of —X and —$CH_2$—X;
and $R_4$ is selected from hydrogen and methyl;
wherein X is selected from the group consisting of phenyl, monosubstituted and disubstituted phenyl, said substituents being selected from the group consisting of chloro, bromo and fluoro;
and the pharmaceutically-acceptable salts thereof.

2. A compound of claim 1, formula I.
3. A compound of claim 2 wherein $R_1$ is —O—$CH_2$—X.
4. A compound of claim 3 wherein R is hydrogen, $R_4$ is methyl and X is 3,4-dichlorophenyl.
5. A compound of claim 2 wherein $R_1$ is —$CH_2$—X.
6. A compound of claim 5 wherein R is hydrogen, $R_4$ is methyl and X is 3,4-dichlorophenyl.
7. A compound of claim 1, formula II.
8. A compound of claim 7 wherein R is hydrogen, $R_4$ is methyl and X is 4-chlorophenyl.
9. A compound of claim 1, formula III.
10. A compound of claim 9, wherein $R_3$ is X.
11. A compound of claim 10, wherein R is hydrogen, $R_4$ is methyl and X is 4-chlorophenyl.
12. A compound of claim 9, wherein $R_3$ is —$CH_2$—X.
13. A compound of claim 12, wherein R is hydrogen, $R_4$ is methyl and X is 3,4-dichlorophenyl.

* * * * *